(12) United States Patent
Chen et al.

(10) Patent No.: US 11,304,662 B2
(45) Date of Patent: Apr. 19, 2022

(54) LUNG-SOUND SIGNAL PROCESSING METHOD, PROCESSING DEVICE, AND READABLE STORAGE MEDIUM

(71) Applicant: BOE TECHNOLOGY GROUP CO., LTD., Beijing (CN)

(72) Inventors: Xue Chen, Beijing (CN); Zhenzhong Zhang, Beijing (CN); Wei Deng, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 801 days.

(21) Appl. No.: 15/941,117

(22) Filed: Mar. 30, 2018

(65) Prior Publication Data

US 2019/0059824 A1 Feb. 28, 2019

(30) Foreign Application Priority Data

Aug. 23, 2017 (CN) .......................... 201710729363.2

(51) Int. Cl.
*A61B 5/00* (2006.01)
*A61B 7/00* (2006.01)
(Continued)

(52) U.S. Cl.
CPC .............. *A61B 5/7264* (2013.01); *A61B 5/08* (2013.01); *A61B 7/003* (2013.01); *G10L 25/18* (2013.01);
(Continued)

(58) Field of Classification Search
CPC .... A61B 5/00; A61B 5/08; A61B 7/00; A61B 5/7264; A61B 7/003; A61B 5/0816; G10L 25/18; G10L 25/21; G10L 25/66
See application file for complete search history.

(56) References Cited

U.S. PATENT DOCUMENTS

| 6,168,568 B1 * | 1/2001 | Gavriely | A61B 5/087 |
| | | | 600/529 |
| 6,738,734 B1 * | 5/2004 | Huang | G06F 17/14 |
| | | | 702/179 |

(Continued)

FOREIGN PATENT DOCUMENTS

| CN | 105913066 A | 8/2016 |
| CN | 106510751 A | 3/2017 |
| WO | 2010132850 A1 | 11/2010 |

OTHER PUBLICATIONS

Marques, Alda & Bruton, Anne & Barney, Anna. (2009). The reliability of lung crackle characteristics in cystic fibrosis and bronchiectasis patients in a clinical setting. Physiological measurement. 30. 903-12. 10.1088/0967-3334/30/9/003 (Year: 2009).*

(Continued)

*Primary Examiner* — Eric J Messersmith
(74) *Attorney, Agent, or Firm* — Dilworth & Barrese, LLP.; Michael J. Musella, Esq.

(57) ABSTRACT

A lung-sound signal processing method, device and computer-readable storage medium. The lung-sound processing method includes: obtaining a lung sound signal; decomposing the lung sound signal, to obtain a crackle-sound component and a respiration-sound component; obtaining an inspiratory-phase period based on the respiration-sound component; extracting a crackle-sound signal located in the inspiratory-phase period from the crackle-sound component; and obtaining at least one feature parameter according to the crackle-sound signal.

19 Claims, 5 Drawing Sheets

(51) Int. Cl.
*G10L 25/18* (2013.01)
*G10L 25/66* (2013.01)
*G10L 25/21* (2013.01)
*A61B 5/08* (2006.01)

(52) U.S. Cl.
CPC .............. *G10L 25/21* (2013.01); *G10L 25/66* (2013.01); *A61B 5/0816* (2013.01)

(56) References Cited

U.S. PATENT DOCUMENTS

| | | | |
|---|---|---|---|
| 2003/0033094 A1 | 2/2003 | Huang | |
| 2006/0247550 A1* | 11/2006 | Thiagarajan | A61B 5/7285 600/528 |
| 2008/0243017 A1* | 10/2008 | Moussavi | G16H 40/63 600/532 |
| 2017/0135644 A1 | 5/2017 | Hsiao et al. | |
| 2017/0135649 A1* | 5/2017 | Kametani | A61B 5/08 |
| 2017/0325779 A1* | 11/2017 | Spina | A61B 5/725 |
| 2018/0177432 A1* | 6/2018 | Au | A61B 7/003 |

OTHER PUBLICATIONS

M. Ono, K. Arakawa, M. Mori, T. Sugimoto and H. Harashima, "Separation of fine crackles from vesicular sounds by a nonlinear digital filter," in IEEE Transactions on Biomedical Engineering, vol. 36, No. 2, pp. 286-291, Feb. 1989, doi: 10.1109/10.16477. (Year: 1989).*

Chen et al., "Identification of Velcro rales based on Hilbert-Huang transform," Physica A: Statistical Mechanics and its Applications, vol. 401, pp. 34-44 (Year: 2014).*

First Office Action dated Mar. 6, 2020 by the Chinese Patent Office in the priority Chinese application No. 201710729363.2 and its English translation.

Enhancement of lung sounds based on empirical mode decomposition and Fourier transform algorithm, Ashok Mondal , Poulami Banerjee, Ajay Somkuwar, Department of Electronics and Communication Engineering, National Institute of Technology, Bhopal, India, Computer methods and programs in biomedicine 139 (Oct. 24, 2016) 119-136.

Study on Method of Heart Sound Signal Extraction Based on EMD and SVD, Thesis submitted to Chongqing University in Partial Fulfillment of the Requirement of Professional Degree, College of Communication Engineering of Chongqing University, Chongqing, China, Yong Xi, Apr. 2016 (Parts 1, 2 and 3).

* cited by examiner

LUNG-SOUND SIGNAL PROCESSING METHOD, PROCESSING DEVICE, AND READABLE STORAGE MEDIUM

The present application claims the priority of the Chinese Patent Application No. 201710729363.2 filed on Aug. 23, 2017, which is incorporated herein by reference in its entirety as part of the disclosure of the present application.

TECHNICAL FIELD

Embodiments of the present disclosure relate to a lung-sound signal processing method, a lung-sound processing device, and a readable storage medium.

BACKGROUND

Auscultatory sounds of lungs are related to pathological conditions of the lungs. Due to different hearing sensitivities of human ears in different frequency bands, as well as a low intensity, short duration and wide bandwidth of crackle sounds in auscultatory sounds, diagnostic results obtained by different doctors based on auscultation may sometimes be inconsistent. Currently, digital auscultation which serves as an auxiliary diagnosis of lung diseases may make up for subjectivity and limitations of auscultation by a doctor.

SUMMARY

At least an embodiment of the disclosure provide a lung-sound signal processing method, comprising: obtaining a lung sound signal; decomposing the lung sound signal, to obtain a crackle-sound component and a respiration-sound component; obtaining an inspiratory-phase period based on the respiration-sound component; extracting a crackle-sound signal located in the inspiratory-phase period from the crackle-sound component; and obtaining at least one feature parameter according to the crackle-sound signal.

For example, the obtaining an inspiratory-phase period based on the respiration-sound component, includes: obtaining a stationary respiration cycle based on the respiration-sound component; and obtaining the inspiratory-phase period from the stationary respiration cycle; wherein the stationary respiration cycle includes an expiratory-phase period and the inspiratory-phase period.

For example, the decomposing the lung sound signal, to obtain the crackle-sound component and the respiration-sound component, includes: decomposing the lung sound signal by using an empirical mode decomposition algorithm, so that the lung sound signal is decomposed into a cumulative sum of a plurality of intrinsic mode functions; calculating a frequency spectrum of each intrinsic mode function from the plurality of intrinsic mode functions; selecting a threshold frequency; summing up intrinsic mode functions whose frequency spectra are greater than the selected threshold frequency, to obtain the crackle-sound component; and summing up intrinsic mode functions whose frequency spectra are less than or equal to the selected threshold frequency, to obtain the respiration-sound component.

For example, the selected threshold frequency is located between 30 hertz and 50 hertz.

For example, the obtaining at least one feature parameter according to the crackle-sound signal, includes: obtaining at least one time-domain feature parameter.

For example, the at least one time-domain feature parameter includes at least one of: a quantity of crackle sounds at an early stage of the inspiratory-phase period, a quantity of crackle sounds at a later stage of the inspiratory-phase period, a quantity of crackle sounds within the inspiratory-phase period, and a ratio of a time duration of the crackle-sound signal to a time length of the inspiratory-phase period.

For example, the obtaining at least one feature parameter according to the crackle-sound signal, includes: obtaining at least one frequency-domain feature parameter.

For example, the at least one frequency-domain feature parameter includes at least one of: a total energy of the crackle-sound signal, and ratios of energies of crackle sounds of respective sub-bands to the total energy.

For example, the lung-sound signal processing method further comprises: obtaining a frequency spectrum function of the crackle-sound signal; obtaining a total bandwidth corresponding to the crackle-sound signal based on the frequency spectrum function; obtaining a plurality of sub-bands based on the total bandwidth; and calculating an energy of crackle sounds of each sub-band in the plurality of sub-bands.

At least an embodiment of the disclosure provide a computer readable storage medium, configured to store computer instructions, the computer instructions, when executed by a processor, causing the processor to implement one or more operations including: obtaining a lung sound signal; decomposing the lung sound signal, to obtain a crackle-sound component and a respiration-sound component; obtaining an inspiratory-phase period based on the respiration-sound component; extracting a crackle-sound signal located in the inspiratory-phase period from the crackle-sound component; and obtaining at least one feature parameter according to the crackle-sound signal.

For example, the computer instructions, when executed by the processor, cause the processor to further implement an operation including: classifying the crackle-sound signal based on the at least one feature parameter.

At least an embodiment of the disclosure provide a lung-sound signal processing device, comprising one or more processors, the one or more processors being configured to run computer instructions so as to execute one or more operations including: obtaining a lung sound signal; decomposing the lung sound signal, to obtain a crackle-sound component and a respiration-sound component; obtaining an inspiratory-phase period based on the respiration-sound component; extracting a crackle-sound signal located in the inspiratory-phase period from the crackle-sound component; and obtaining at least one feature parameter according to the crackle-sound signal.

For example, the lung-sound signal processing device further comprises a classifier, the classifier being configured to classify the crackle-sound signal based on the at least one feature parameter.

For example, the classifier is configured to classify the crackle-sound signal based on the at least one feature parameter by using a tree-based method.

For example, the at least one feature parameter includes at least one of a frequency-domain feature parameter and a time-domain feature parameter.

For example, the at least one time-domain feature parameter includes at least one of: a quantity of crackle sounds at an early stage of the inspiratory-phase period, a quantity of crackle sounds at a later stage of the inspiratory-phase period, a quantity of crackle sounds within the inspiratory-phase period, and a ratio of a time duration of the crackle-sound signal to a time length of the inspiratory-phase period.

For example, the at least one of the frequency-domain feature parameter includes at least one of: a total energy of the crackle-sound signal, and ratios of energies of crackle sounds of respective sub-bands to the total energy.

For example, the obtaining the inspiratory-phase period based on the respiration-sound component, includes: obtaining a stationary respiration cycle based on the respiration-sound component; and obtaining the inspiratory-phase period from the stationary respiration cycle; wherein the stationary respiration cycle includes an expiratory-phase period and the inspiratory-phase period.

For example, the decomposing the lung sound signal, to obtain the crackle-sound component and the respiration-sound component, includes: decomposing the lung sound signal by using an empirical mode decomposition algorithm, so that the lung sound signal is decomposed into a cumulative sum of a plurality of intrinsic mode functions; calculating a frequency spectrum of each intrinsic mode function from the plurality of intrinsic mode functions; selecting a threshold frequency; summing up intrinsic mode functions whose frequency spectra are greater than the selected threshold frequency, to obtain the crackle-sound component; and summing up intrinsic mode functions whose frequency spectra are less than or equal to the selected threshold frequency, to obtain the respiration-sound component.

For example, the selected threshold frequency is located between 30 hertz and 50 hertz.

BRIEF DESCRIPTION OF THE DRAWINGS

In order to illustrate the technical solutions in the embodiments of the present disclosure more clearly, the drawings needed to be used in the description of the embodiments will be briefly described in the following; and it is obvious that the drawings described below are only related to some embodiments of the present disclosure, and not intended to be limitative to the disclosure.

DETAILED DESCRIPTION

Hereinafter, the purposes, the technical solutions and the advantages of the embodiments of the present disclosure will be described in a clearly and fully understandable way in conjunction with the drawings related to the embodiments of the present disclosure. It is obvious that the described embodiments are just a part but not all of the embodiments of the present disclosure. Based on embodiments of the present disclosure, all other embodiments obtained by those skilled in the art without making other inventive work should be within the scope of the present disclosure.

Unless otherwise defined, technical terms or scientific terms used in the present disclosure should be of general meaning as understood by those ordinarily skilled in the art. "First", "second" and similar words used in the present disclosure do not represent any sequence, quantity or importance and merely intend to differentiate different composite parts. The terms "comprises," "comprising," "includes," "including," etc., are intended to specify that the elements or the objects stated before these terms and encompass the elements or the objects and equivalents thereof listed after these terms, but do not preclude the other elements or objects.

Figure 1:
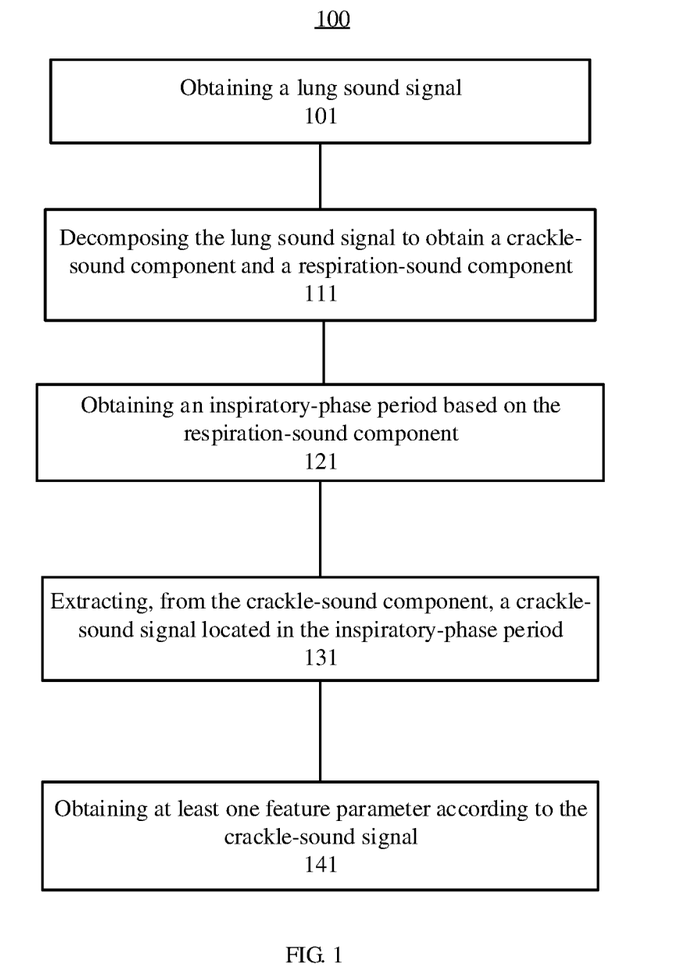
FIG. 1 is a flow chart of a lung-sound signal processing method provided by an embodiment of the present disclosure.

FIG. 1 is a lung-sound signal processing method 100 provided by an embodiment of the present disclosure. The lung-sound signal processing method 100 may comprise, but is not limited to:

Step 101: obtaining a lung sound signal;

Step 111: decomposing the lung sound signal to obtain a crackle-sound component and a respiration-sound component;

Step 121: obtaining an inspiratory-phase period based on the respiration-sound component;

Step 131: extracting, from the crackle-sound component, a crackle-sound signal located in the inspiratory-phase period; and Step 141: obtaining at least one feature parameter according to the crackle-sound signal.

In some embodiments, the lung sound signal obtained in step 101 is a lung sound signal read with a lung sound signal detector (for example, a stethoscope or a PvDF piezoelectric sensor), or a lung sound signal obtained after pre-processing the read lung sound signal. For example, the pre-processing includes sampling processing and filtering processing. For another example, a sampling time for the sampling processing is 10 seconds, and a sampling frequency fs may be 10000 Hz.

In some embodiments, a band-pass filter is used for performing the filtering processing. For example, specifically an 8-order Butterworth band-pass filter may be used, and a passband may be 50 Hz to 2000 Hz. By performing band-pass filtering on the signal obtained from sampling, a heart sound signal, power frequency interference and other noises may be removed.

For example, an empirical mode algorithm may be used for decomposing the lung sound signal. In some embodiments, in step 111, the lung sound signal is decomposed, for example, by methods such as wavelet domain filtering, blind source separation, wavelet packet decomposition and singular value decomposition, etc.

In some embodiments, in step 121, the step of obtaining an inspiratory-phase period based on the respiration-sound component may include: obtaining a stationary respiration cycle based on the respiration-sound component; and obtaining the inspiratory-phase period from the stationary respiration cycle; where the stationary respiration cycle includes an expiratory-phase period and the inspiratory-phase period. For example, the so-called stationary respiration cycle refers to a respiration cycle with a relatively stationary power curve in a plurality of respiration cycles (for example, FIG. 3 and illustration of FIG. 3 may be referred to).

Figure 2:
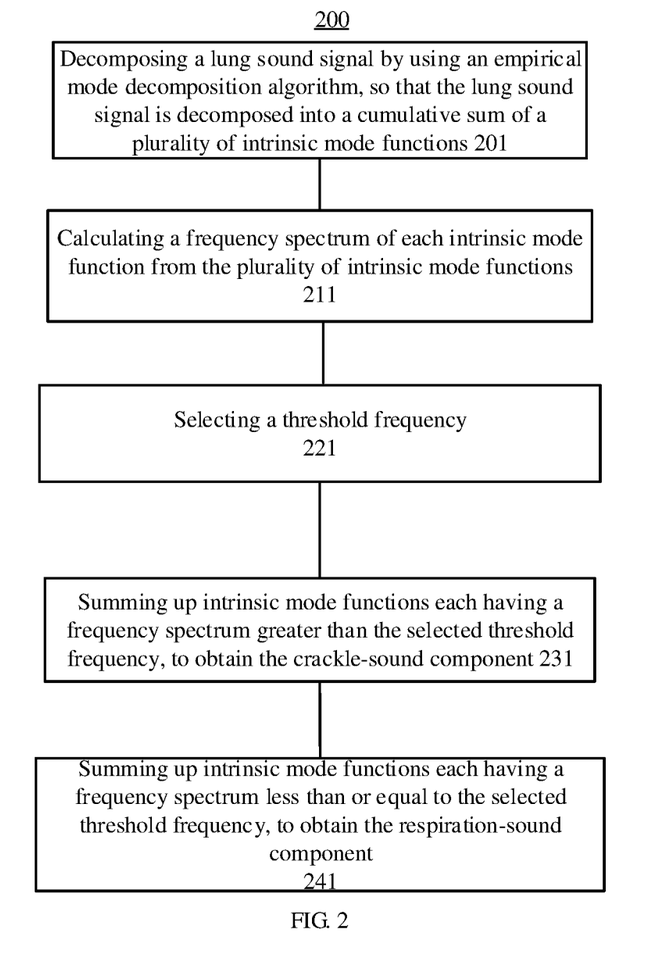
FIG. 2 is a flow chart of a method for calculating a crackle-sound component and a respiration-sound component provided by an embodiment of the present disclosure.

With reference to FIG. 2, an embodiment of the present disclosure provides a method 200 for calculating a crackle-sound component and a respiration-sound component. For example, the step 111 in FIG. 1 may be implemented by using the method 200. For example, the method 200 may comprise, but is not limited to:

Step 201: decomposing the lung sound signal by using an empirical mode decomposition algorithm, so that the lung sound signal is decomposed into a cumulative sum of a plurality of intrinsic mode functions;

Step 211: calculating a frequency spectrum of each intrinsic mode function from the plurality of intrinsic mode functions;

Step 221: selecting a threshold frequency;

Step 231: summing up intrinsic mode functions (for example, two or more intrinsic mode functions) each having a frequency spectrum greater than the selected threshold frequency, to obtain the crackle-sound component; and Step 241: summing up intrinsic mode functions (for example, two or more than two intrinsic mode functions) each having a frequency spectrum less than or equal to the selected threshold frequency, to obtain the respiration-sound component. For example, a range of the threshold frequency may be greater than or equal to 30 hertz and less than or equal to 50 hertz (i.e., [30 Hz, 50 Hz]).

Hereinafter, by taking a case where the 50 Hz is served as the selected threshold frequency as an example, the process of obtaining the crackle-sound component and the respiration-sound component is illustrated in conjunction with FIG. 3.

Figure 3:
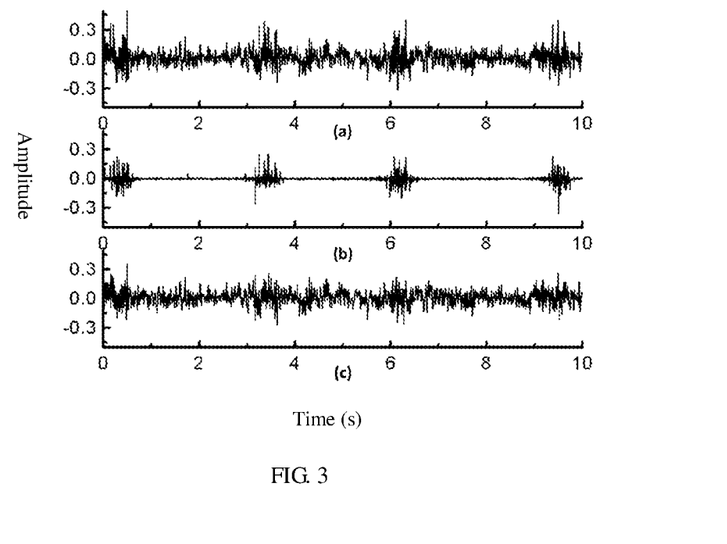
FIG. 3 shows a schematic diagram of an exemplary lung sound signal as well as a crackle-sound component and a respiration-sound component obtained after the lung sound signal is decomposed.

Part (a) in FIG. 3 is a schematic diagram of an obtained lung sound signal, part (b) in FIG. 3 is a schematic diagram of a crackle-sound component obtained after the lung sound signal of part (a) is decomposed, and part (c) in FIG. 3 is a schematic diagram of a respiration-sound component obtained after the lung sound signal of part (a) is decomposed.

Firstly, the lung sound signal after filtering (as shown in part (a) of FIG. 3) is decomposed by using the empirical mode decomposition (EMD) algorithm. A lung sound signal s(t) is decomposed into a cumulative sum of a series of intrinsic mode functions (IMFs) by self-adaptive decomposition (as shown in Formula (1) below), wherein frequencies of respective intrinsic mode functions (IMFs) gradually decrease, and each intrinsic mode function (IMF) has its own physical meaning (for example, some intrinsic mode functions characterize the heart sound signal, and some intrinsic mode functions characterize the breath sound signal).

$$s(t) = \sum_{k=1}^{N} IMF_k(t) + r_N(t) \quad (1)$$

The above-described s(t) denotes a lung sound signal that is not decomposed, N denotes the number of intrinsic mode functions (IMFs) obtained by decomposition (i.e., the number of layers into which the signal s(t) is decomposed), and $r_N(t)$ denotes a signal residue.

For example, when a certain intrinsic mode function obtained by decomposition does not have any oscillating property, that is, when the function has only one zero-crossing point, the empirical mode decomposition performed on the lung sound signal is terminated, and a specific value of N may be obtained at this point.

Then, fast Fourier transform is used for calculating frequency spectra of respective intrinsic mode functions (IMFs), and a cumulative sum of intrinsic mode functions (IMFs) whose frequencies are distributed above 50 Hz are selected to be the crackle-sound component (for example, with reference to Formula (2)), and a cumulative sum of the remaining intrinsic mode functions (IMFs) is taken as the respiration-sound component (for example, with reference to Formula (3)), namely:

$$x_{cra}(t) = \sum_{k=1}^{n} IMF_k(t) \quad (2)$$

$$x_{res}(t) = \sum_{k=n+1}^{N} IMF_k(t) + r_N(t) \quad (3)$$

The above-described $x_{cra}(t)$ denotes the crackle-sound component, $x_{res}(t)$ denotes the respiration-sound component, a frequency corresponding to a peak of a Fourier spectrum of $IMF_k(t)$ in Formula (2) is greater than 50 Hz (1≤k≤n), and a frequency corresponding to a peak of a Fourier spectrum of $IMF_k(t)$ in Formula (3) is less than 50 Hz (n+1≤k≤N).

Since the breath sound signals and heartbeat sounds and other physiological or non-physiological noises are mixed together, a process for determining the above-described frequency threshold of 50 Hz is relatively complicated. The non-linear, non-stationary lung sound signal is processed by a frequency value of 50 Hz, which may effectively separate the crackle-sound component and the respiration-sound component included in the lung sound signal.

Hereinafter, the process of obtaining the inspiratory-phase period of step 121 and the process of extracting the crackle-sound signal of step 131 in FIG. 1 will be illustrated below in conjunction with FIG. 4 and Formula (4). Of course, the inspiratory-phase period and the crackle-sound signal may also be obtained according to other approaches, which will not be limited in the present disclosure here.

Figure 4:
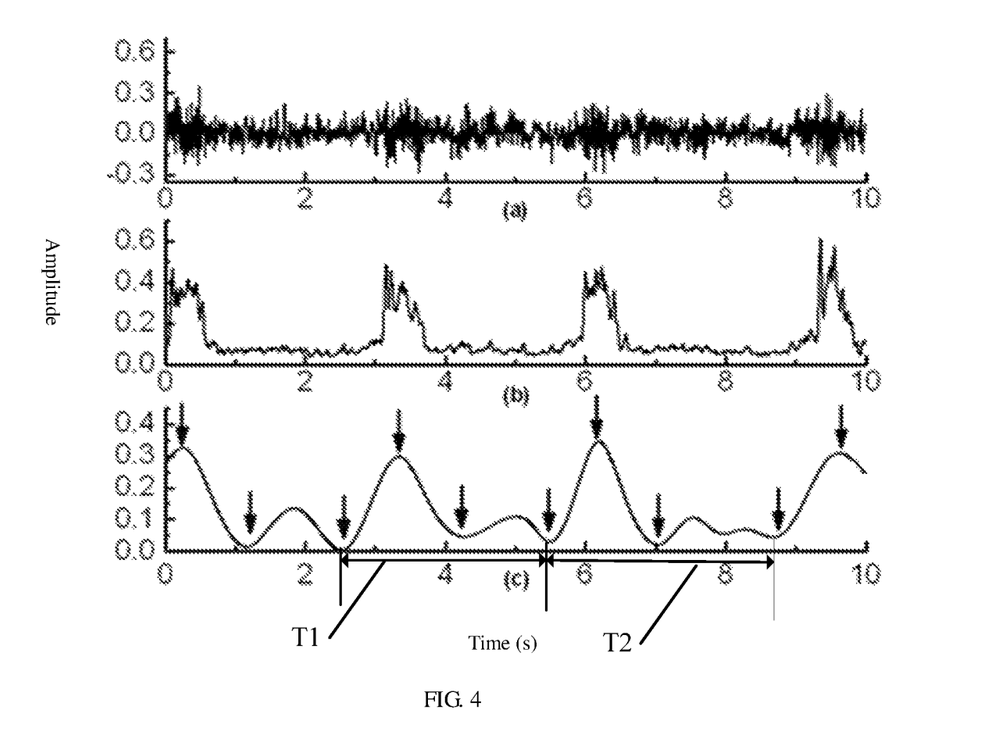
FIG. 4 shows an exemplary respiration-sound component, as well as an average power curve of the respiration-sound component, and a smoothed power curve after the average power curve is smoothed.

Part (a) in FIG. 4 is the respiration-sound component shown by part (c) in FIG. 3, part (b) in FIG. 4 is an average power curve corresponding to the respiration-sound component shown by part (a) in FIG. 4, and part (c) in FIG. 4 is a smoothed power curve obtained after the average power curve of part (b) in FIG. 4 is smoothed. All of the respiratory phase vertexes (i.e., peaks) and respiratory switching points (i.e., bottom points at the valleys) are shown on the smoothed power curve of part (c) in FIG. 4.

Firstly, a Hilbert-Huang Transform (HHT) time frequency spectrum of the respiration-sound component (i.e., part (a) in FIG. 4) is calculated, and is cumulatively averaged along a frequency direction to obtain a HHT-based average power curve (i.e., as shown by part (b) in FIG. 4). For example, as shown in Formula (4):

$$p_{average}(t) = \sum_{f_k=f_{low}}^{f_{high}} |H_{res}(f_k, t)|^2 / (f_{high} - f_{low}) \quad (4)$$

Here, $f_{high}$=450 Hz, $f_{low}$=150 Hz, $H_{res}(f_k,t)$ is an amplitude of a point (t, $f_k$) on the HHT time frequency spectrum of $x_{res}(t)$. A main reason for selecting a frequency band of 150 Hz to 450 Hz as the frequency band in the above-described Formula (4) is that, within the range of this frequency band, energy difference between the crackle-sound component corresponding to the inspiratory-phase period and the respiration-sound component corresponding to the expiratory-phase period is the most obvious.

Then, smoothing is performed on the calculated average power curve (as shown by part (b) of FIG. 4) by using a sliding averaging method (for example, with a window width=50 ms); peak points of the smoothed average power curve are identified as the inspiratory phase vertexes (for example, the peak points to which arrows of part (c) in FIG. 4 are directed), and valley points of the smoothed average power curve are identified as the switching points of the respiratory phase (for example, the valley points to which arrows of part (c) in FIG. 4 are directed), so as to obtain information of the respiratory phase (i.e., to obtain all peak points and valley points); and then a crackle-sound component in an inspiratory phase of a stationary respiration cycle is extracted. For example, a plurality of inspiratory phase vertexes and switching points of respiration (expiration and inspiration) in a sampling cycle are obtained according to the respiration-sound component (for example, points to which respective arrows of part (c) in FIG. 4 are directed); and secondly, a time window between a starting time of a waveform where an inspiratory phase vertex is located and an ending time of a waveform where a switching point of the respiratory phase is located is taken as a respiration cycle (for example, part (c) of FIG. 4 shows two respiration cycles T1 and T2 in a sampling cycle of 10 seconds). For example, along the time direction, each respiration cycle starts from a first switching point of the respiratory phase, passes through an inspiratory phase vertex and a second switching point of the respiratory phase, and ends at a third switching point of the respiratory phase. Finally, segments of the obtained smoothed power curve which correspond to respective respiration cycles are compared with one another (for example, segments of the average power curve corresponding to the respiration cycles T1 and T2 in part (c) of FIG. 4 are compared with one another), and a respiration cycle corresponding to a relatively stationary segment of the average power curve is taken as a stationary respiration cycle. For example, in part (c) of FIG. 4, a segment of the smoothed power curve corresponding to the respiration cycle T1 is more stationary than a segment of the smoothed power curve corresponding to the respiration cycle T2, and therefore, the respiration cycle T1 is selected as the stationary respiration cycle of the sampling period of 10 seconds.

In some embodiments, the inspiratory-phase period is a time duration for which the inspiratory phase lasts within the stationary respiration cycle.

It should be noted that, in some embodiments, the crackle-sound component of the inspiratory-phase period in the stationary respiration cycle T1 in part (c) of FIG. 4 is taken as the crackle-sound signal for subsequent analysis of feature parameters. For example, the crackle-sound signal may be a portion of the crackle-sound component $x_{cra}(t)$ in the above-described Formula (2), and this portion of the crackle-sound component is located in the inspiratory-phase period of the stationary respiration cycle T1. For example, in subsequent FIG. 5 and FIG. 6, the portion of the crackle-sound component in the inspiratory-phase period of the stationary respiration cycle T1 in part (c) of FIG. 4 is taken as the crackle-sound signal, for further analysis and processing.

In some embodiments, in step 141 of FIG. 1, the obtaining at least one feature parameter according to the crackle-sound signal (for example, the portion of the crackle-sound component corresponding to the inspiratory-phase period of the stationary respiration cycle T1 in part (c) of FIG. 4 is the crackle-sound signal), includes: obtaining at least one time-domain feature parameter. The at least one time-domain feature parameter includes at least one of: the number of crackle sounds at an early stage of the inspiratory-phase period, the number of crackle sounds at a later stage of the inspiratory-phase period, the number of crackle sounds within the inspiratory-phase period, and a ratio of a time duration of the crackle-sound signal to a length of the inspiratory-phase period.

In some embodiments, an early stage of an inspiratory-phase period is a time period located in an anterior position in the inspiratory-phase period, and a time length of the time period may be set according to actual situations. A later stage of an inspiratory-phase period is a time period located in a posterior position in the inspiratory-phase period, and a time length of the time period may be set according to actual situations. For example, an inspiratory-phase period is divided equally into two independent periods from the middle, where a fore time period may be taken as the early stage of the inspiratory-phase period, and a back time period may be taken as the later stage of the inspiratory-phase period. For example, an inspiratory-phase period may also be divided into three time periods, which are respectively referred to as a first time period, a second time period and a third time period according to a sequential time order in which the three time periods appear, where the first time period is taken as the early stage of the inspiratory-phase period, and the third time period is taken as the later stage of the inspiratory-phase period.

Hereinafter, a process of obtaining time-domain feature parameters will be illustrated in conjunction with Formula (5) as well as FIG. 5 and FIG. 6.

Figure 5:
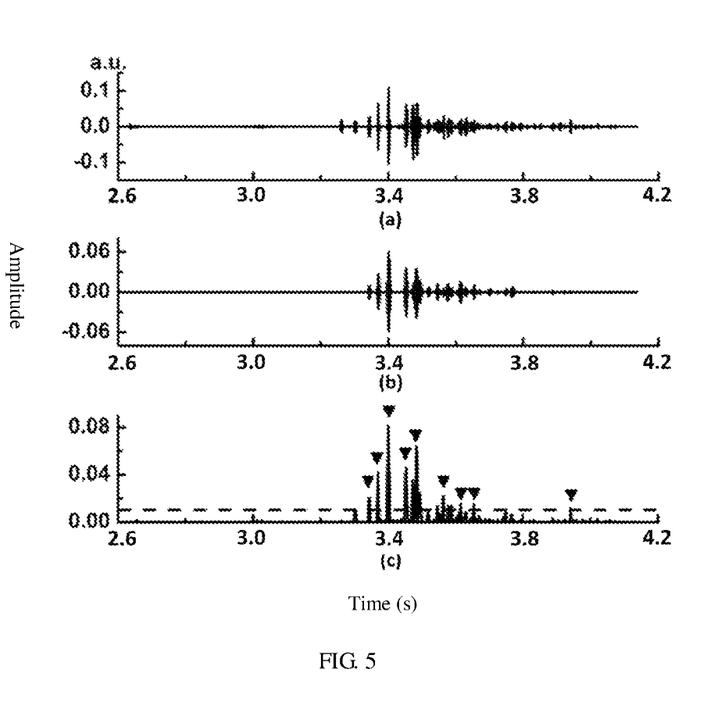
FIG. 5 shows a diagram of an amplitude of an exemplary crackle-sound signal, a diagram of a time-domain amplitude of a first intrinsic mode function obtained by decomposing the crackle-sound signal as well as a diagram of an instantaneous amplitude of the first intrinsic mode function.

Part (a) of FIG. 5 shows an amplitude diagram of the crackle-sound signal (for example, the crackle-sound signal is the portion the crackle-sound component corresponding to the inspiratory-phase period included in the stationary respiration cycle T1 in part (c) of FIG. 4), part (b) in FIG. 5 is a time-domain amplitude diagram of a first intrinsic mode function (IMF) obtained by decomposing the crackle-sound signal in part (a) in FIG. 5, and part (c) in FIG. 5 is an instantaneous amplitude diagram of the first intrinsic mode function corresponding to part (b) in FIG. 5. A dashed line in part (c) of FIG. 5 is used for indicating that crackle sounds in the crackle-sound component whose amplitudes are greater than a threshold value (e.g., 0.01) are selected as a constituent portion of the crackle-sound signal, for example, the crackle sounds indicated by triangular patterns in part (c) in FIG. 5 are crackle sounds in the crackle-sound component whose amplitudes are greater than 0.01, and these crackle sounds together form the crackle-sound signal. In some embodiments, counting the number of related crackle sounds may include counting the number of crackle sounds whose amplitudes are greater than the threshold shown by part (c) in FIG. 5. For example, counting the number of crackle sounds at the early stage of the inspiratory-phase period and the number of crackle sounds at the later stage of the inspiratory-phase period may also include counting the number of crackle sounds whose amplitudes are greater than 0.01 at the early stage of the inspiratory-phase period and counting the number of crackle sounds whose amplitudes are greater than 0.01 at the later stage of the inspiratory-phase period, respectively.

Figure 6:
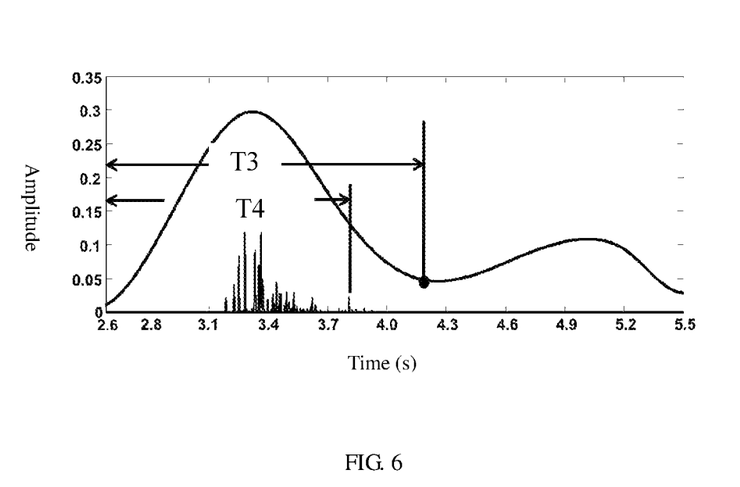
FIG. 6 is a schematic diagram of an inspiratory-phase period provided by an embodiment of the present disclosure.

FIG. 6 shows an image obtained by superimposing the amplitude of portion (c) in FIG. 5 with the respiration-sound component in the period of the stationary respiration cycle T1 shown by part (c) in FIG. 4. In addition, T3 in FIG. 6 denotes the inspiratory-phase period of the stationary respiration cycle T1, and T4 denotes a time duration from the starting time of the stationary respiration cycle T1 (which is also the starting time of the inspiratory-phase period T3) to the time when the last crackle sound (whose amplitude is greater than the threshold value) appears within the inspiratory-phase period T3.

For example, an ending time ratio (ETR) of the ending time of the crackle-sound signal to the inspiratory-phase period is taken as another time-domain feature parameter, that is:

$$ETR = \frac{T_{ending}}{T_{inspiration}}. \quad (5)$$

The above-described $T_{ending}$ (i.e., T4 in FIG. 6) denotes the time duration from the starting time of the stationary respiration cycle T1 to the time when the last crackle sound appears within the inspiratory-phase period, $T_{inspiration}$ denotes the time duration of the entire inspiratory-phase period (i.e., T3 in FIG. 6).

In some embodiments, in step 141, the obtaining at least one feature parameter according to the crackle-sound signal, includes: obtaining at least one frequency-domain feature parameter. The at least one frequency-domain feature parameter includes at least one of: a total energy of the crackle-sound signal, and ratios of crackle sound energies of respective sub-bands to the total energy of the crackle-sound signal. For example, the obtaining at least one frequency-domain feature parameter may include: obtaining the total energy of the crackle sounds; and/or obtaining the ratios of the crackle sound energies of the respective sub-bands to the total energy.

In some embodiments, the obtaining the total energy of the crackle sounds, may include: calculating a frequency spectrum function of the crackle sounds within the inspiratory-phase period; obtaining a distribution frequency band of the crackle sounds based on the frequency spectrum function; and calculating the total energy of the crackle sounds located in the distribution frequency band.

In some embodiments, the obtaining the ratios of the energies of respective sub-bands to the total energy, may include: calculating the total energy of the crackle-sound signal; obtaining the frequency spectrum function of the crackle-sound signal; obtaining the distribution frequency band of the crackle sounds based on the frequency spectrum function; dividing the distribution frequency band into a plurality of sub-bands; calculating an energy of the crackle sounds included in each sub-band of the plurality of sub-bands; and calculating a ratio of the energy of the crackle sounds in the each sub-band to the total energy.

In some embodiments, the step of obtaining the sub-bands may include: obtaining the frequency spectrum function of the crackle-sound signal; obtaining a total bandwidth corresponding to the crackle-sound signal based on the frequency spectrum function; and obtaining a plurality of sub-bands based on the total bandwidth. For example, the total bandwidth may be obtained by using Fourier transform. For example, the total bandwidth may be divided equally into a plurality of sub-bands. For example, a frequency band where a primary portion of the energy is located may be obtained firstly, the frequency band where the primary portion of the energy is located is divided into a plurality of sub-bands, and a width of the frequency band where the primary portion of the energy is located is less than or equal to the total bandwidth. For example, the primary portion of the energy may be 70%, 80%, 90% of the total energy or another proportional value. For example, the frequency band where the primary portion of the energy is located may occupy 80% or 90% of the total frequency band or another proportional value.

Hereinafter, a process of obtaining frequency-domain feature parameters will be illustrated in details, by taking a case that the frequency band where the primary portion of the energy is located as a basis for dividing into the sub-bands as an example, in conjunction with Formula (6), Formula (7) and Formula (8).

Firstly, an HHT marginal spectrum of the crackle-sound component within the inspiratory-phase period (i.e., the crackle-sound signal) is calculated, with a calculation formula as follows:

$$h(f) = \int_{t_1}^{t_2} H_{cra}(f, t)dt \quad (6)$$

The above-described $H_{cra}(f,t)$ is the HHT time-frequency spectrum of the crackle-sound signal (the crackle-sound signal is a portion of the crackle-sound component $x_{cra}(t)$ located in the inspiratory-phase period of the stationary respiration cycle T1), h(f) denotes the HHT marginal spectrum of the crackle-sound signal, $t_1$ denotes the starting time of the selected inspiratory-phase period, and $t_2$ denotes the ending time of the selected inspiratory-phase period.

Then, the total energy of the crackle-sound signal is calculated according to a formula below, as a first frequency-domain feature parameter:

$$E = \int_{f_0}^{f_T} h(f)df \quad (7)$$

The above-described E denotes the total energy of the crackle-sound signal, h(f) denotes the HHT marginal spectrum of the crackle-sound signal $x_{cra}(t)$, $f_0$=50 Hz, $f_T$=1550 Hz. 50 Hz and 1550 Hz are respectively selected as an upper limit and an integral lower limit of the integral in Formula (7), because the primary portion of the energy of the crackle-sound signal is distributed within the range of 50 Hz to 1550 Hz.

Finally, the primary energy frequency band (50 Hz to 1550 Hz) of the crackle-sound signal is equally divided into 15 sub-bands by a step length of 100 Hz, and an energy weight (EW) of each sub-band relative to the total energy is calculated according to a formula below, as other 15 frequency-domain feature parameters.

$$EW_{FB} = \int_{f_1}^{f_2} h(f)df/E \quad (8)$$

The above-described $EW_{FB}$ denotes an energy weight on a different sub-band, E denotes the total energy of the crackle-sound signal, $f_1$ and $f_2$ are cutoff frequencies of the different sub-band, f1=50+(n−1)×100, f2=50+n×100, and 1≤n≤15.

In some embodiments, the above-described extracted feature parameters include: the total energy E of the crackle-sound signal, energy weights $EW_{FB}$ of the crackle sounds in different sub-bands in the crackle-sound signal (for example, 15 feature parameters corresponding to the above-described 15 sub-bands), the number of crackle sounds occurring at the early stage of the inspiratory-phase period, the number of crackle sounds occurring at the later stage of the inspiratory-phase period, the number of crackle sounds occurring in the entire inspiratory phase, and the ending time ratio (ETR) of the ending time of the crackle-sound signal to the inspiratory-phase period, which has a total of 20 feature parameters (including 15 feature parameters related to the sub-bands). All or some of the above-described 20 feature parameters may be input into a trained classifier, to classify and recognize the crackle-sound signal, and output a recognition result.

In some embodiments, the above-described recognition result is used for characterizing a lung-sound health condition of a testee. That is to say, the recognition result is used for characterizing whether the testee is healthy or not, and whether the testee has a lung disease.

In some embodiments, the recognition result may also be a specific disease of a patient with a lung disease. For example, the plurality of feature parameters as described above is taken as feature vectors input to the classifier, then the classifier further outputs the recognition result indicating a specific lung disease from which the patient suffers, according to features of peculiar crackle rales of a patient with an interstitial lung disease, peculiar bubbling rales of a patient with a chronic obstructive pulmonary disease, and peculiar bubbling rales of a patient with a chronic heart failure.

In some embodiments, the data corresponding to the plurality of feature parameters as described above may be taken as training data, and the classifier may be trained based on the training data.

An embodiment of the present disclosure further provides a computer readable storage medium having computer instructions stored thereon, and the computer instructions, when executed by a processor, implement one or more operations including:

obtaining a lung sound signal;

decomposing the lung sound signal to obtain a crackle-sound component and a respiration-sound component;

obtaining an inspiratory-phase period based on the respiration-sound component;

extracting a crackle-sound signal located in the inspiratory-phase period from the crackle-sound component; and obtaining at least one feature parameter according to the crackle-sound signal.

In some embodiments, the computer instructions, when executed by the processor, are further used for implementing an operation including: classifying the crackle-sound signal based on the at least one feature parameter.

In some embodiments, the computer-readable storage medium may be used for storing and/or transferring data and/or instructions executable to implement the methods and the processes described herein. For example, the computer-readable storage medium may include any type of volatile or non-volatile storage device or a combination thereof, for example, a static random access memory (SRAM), an electrically erasable programmable read only memory (EEPROM), an erasable programmable read-only memory (EPROM), a programmable read-only memory (PROM), a read-only memory (ROM), a magnetic memory, a solid-state memory, a flash memory, a magnetic disk or an optical disk.

In some embodiments, various aspects of the instructions as described herein may be propagated in a transient manner through pure signals (e.g., electromagnetic signals, optical signals, etc.) that are not maintained by a physical device for at least a finite duration of time. In addition, data and/or other forms of information related to the present disclosure may be propagated through pure signals.

Figure 7:
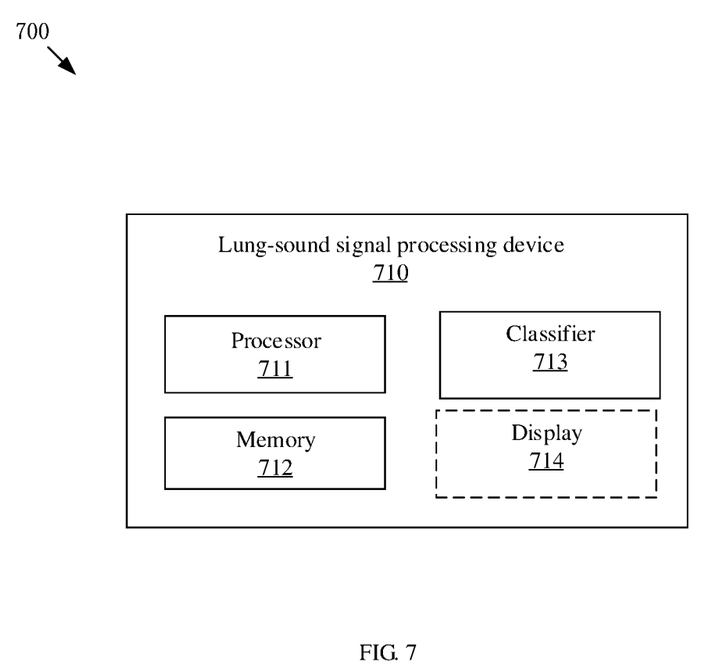
FIG. 7 is a composition block diagram of a lung-sound signal processing device provided by an embodiment of the present disclosure.

As shown in FIG. 7, an embodiment of the present disclosure provides a lung-sound signal processing device 700. The lung-sound processing device 700 may comprise: one or more processors 711, the one or more processors 711 being configured to execute computer instructions so as to implement one or more operations including:

reading a lung sound signal;

decomposing the lung sound signal to obtain a crackle-sound component and a respiration-sound component;

obtaining an inspiratory-phase period based on the respiration-sound component;

extracting a crackle-sound signal located in the inspiratory-phase period from the crackle-sound component; and obtaining at least one feature parameter according to the crackle-sound signal.

In some embodiments, the signal processing device may further comprise a memory 712, the memory 712 being connected with the processor 711. The memory 712 stores the computer instructions, and the computer instructions, when executed by the processor, implement one or more operations of: reading a lung sound signal; decomposing the lung sound signal to obtain a crackle-sound component and a respiration-sound component; obtaining an inspiratory-phase period based on the respiration-sound component; extracting a crackle-sound signal located in the inspiratory-phase period from the crackle-sound component; and obtaining at least one feature parameter according to the crackle-sound signal.

In some embodiments, the lung-signal processing device may further comprise a classifier 713. The classifier 713 is configured to classify the crackle-sound signal based on the at least one feature parameter.

In some embodiments, the lung sound processing device 700 may further comprise at least one lung sound signal detector, and the lung sound signal detector may be configured to obtain the lung sound signal. Of course, the lung sound signal detector may also not be included in the lung sound processing device, but may communicate with the lung sound processing device 700 via wired or wireless connection.

For example, the processor may be a central processing unit (CPU) or a field programmable logic array (FPGA) or a single chip microcomputer (MCU) or a digital signal processor (DSP) or an application specific integrated circuit (ASIC), or another logical computing device having data processing capabilities and/or program execution capabilities. One or more processors may be configured to simultaneously execute one or more steps as described above with a processor group for parallel computing, or may be configured to execute some of the one or more steps as described above with some of the processors, and execute other steps of the one or more steps as described above with the other processors, and the like.

For example, the computer instructions include one or more processor operations defined by an instruction set architecture corresponding to the processor, and these computer instructions may be logically included and represented by one or more computer programs.

In some embodiments, the classifier 713 is configured to classify the crackle-sound signal according to the at least one feature parameter based on a tree-based method.

For example, the classifier 713 may be a decision trees classifier, or a random forests classifier, or a boosted trees classifier, or a classifier being improved based on the above-described classifiers (of, e.g., Bootstraping, Adaboosting and other algorithms).

In addition, the classifier may also be implemented based on other methods, for example, a machine-learning based method, a neural-network based method, and the like.

In some embodiments, the memory 712 and the processor 711 may be provided on a same terminal. For example, the terminal may also include a display. For example, the display may be an LED display, an LCD display, and the like.

In some embodiments, the memory 712, the processor 711 and the classifier 713 are provided in one terminal. The classifier-related instructions are also stored in the memory 712.

In some embodiments, a sensor is used for converting the lung sound signal obtained from the stethoscope into an electrical signal, and the obtained electrical signal is transmitted to the processor 513 via a wired or wireless network.

In some embodiments, the display 714 may be configured to output and display a classification result of the classifier 713.

In some embodiments, the classifier is configured to read at least one feature parameter, where the feature parameter includes at least one of a frequency-domain feature parameter and a time-domain feature parameter. For example, at least one of the frequency-domain feature parameter and the time-domain feature parameter is input to the classifier for classification; or the time-domain feature parameter and the frequency-domain feature parameter are input to the classifier at a same time for classification. For example, the time-domain feature parameter may include at least one of the number of crackle sounds at the early stage of the inspiratory-phase period, the number of crackle sounds at the later stage of the inspiratory-phase period, the number of crackle sounds within the inspiratory-phase period, and the ratio of the time duration of the crackle-sound signal to the length of the inspiratory-phase period.

With reference to FIG. 1 to FIG. 6, similar description of the lung-sound signal processing device 700 will not be repeated here.

To sum up, the embodiments of the present disclosure provide the lung-sound signal processing method and device. The method and device firstly perform filtering and other pre-processing on the collected lung sound signal, then perform decomposition on the lung sound signal, select IMFs distributed in the crackle sound frequency band to accumulate the IMFs so as to obtain the crackle-sound component, accumulate the remaining IMFs so as to obtain the respiration-sound component, and calculate the average power curve of the respiration-sound component to obtain the information of the respiratory phase. The crackle-sound component of the inspiratory-phase period of one stationary respiration cycle is extracted as the crackle-sound signal. The crackle-sound signal is used for extracting the total energy E of the crackle sounds in the inspiratory phase, the energy weights $EW_{FB}$ of the crackle sounds in different frequency bands, the number of crackle sounds occurring at the early stage/the later stage of the inspiratory-phase period, the number of crackle sounds in the entire inspiratory phase, the ending time ratio (ETR) of the ending time of the crackle sounds to the inspiratory phase, and other feature parameters. These feature parameters will be input to the random forests classifier for automatic classification and identification, so as to assist a doctor in diagnosis. The embodiments of the present disclosure provide a method and device for effectively distinguishing the peculiar crackle rales of the patient with the interstitial lung disease, the peculiar bubbling rales of the patient with the chronic obstructive pulmonary disease, and the peculiar bubbling rales of the patient with the chronic heart failure, which provides auxiliary information for a doctor in diagnosis, and has a good clinical application value.

The accompanying drawings of the embodiments of the present disclosure only relate to structures related to the embodiments of the present disclosure. Other structures may be referred to in conventional designs. Without conflict, various embodiments of the present disclosure and various features of the various embodiments may be combined with each other to obtain new embodiments.

What are described above is related to the illustrative embodiments of the disclosure only and not limitative to the scope of the disclosure; any changes or replacements easily for those technical personnel who are familiar with this technology in the field to envisage in the scopes of the disclosure, should be in the scope of protection of the present disclosure. Therefore, the scopes of the disclosure are defined by the accompanying claims.

The invention claimed is:

1. A computer-implementing lung-sound signal processing method, comprising:
obtaining a lung sound signal from a lung sound signal detector;
decomposing the lung sound signal by using an empirical mode decomposition algorithm, to obtain a crackle-sound component and a respiration-sound component;
obtaining an inspiratory-phase period based on the respiration-sound component;
extracting a crackle-sound signal located in the inspiratory-phase period from the crackle-sound component; and
obtaining at least one feature parameter according to the crackle-sound signal,
wherein the obtaining at least one feature parameter according to the crackle-sound signal includes: obtaining at least one time-domain feature parameter, the at least one time-domain feature parameter includes an ending time ratio (ETR) of an ending time of the crackle-sound signal to the inspiratory-phase period, wherein the ETR is calculated as:

$$ETR = \frac{T_{ending}}{T_{inspiration}}$$

wherein $T_{ending}$ denotes a time duration from a starting time of a stationary respiration cycle to a time when a last crackle sound appears within the inspiratory-phase period, $T_{inspiration}$ denotes a time duration of the inspiratory-phase period.

2. The lung-sound signal processing method according to claim 1, wherein the obtaining an inspiratory-phase period based on the respiration-sound component, includes:
obtaining the stationary respiration cycle based on the respiration-sound component; and
obtaining the inspiratory-phase period from the stationary respiration cycle;
wherein the stationary respiration cycle includes an expiratory-phase period and the inspiratory-phase period.

3. The lung-sound signal processing method according to claim 1, wherein the decomposing the lung sound signal by using an empirical mode decomposition algorithm, to obtain the crackle-sound component and the respiration-sound component, includes:
decomposing the lung sound signal by using an empirical mode decomposition algorithm, so that the lung sound signal is decomposed into a cumulative sum of a plurality of intrinsic mode functions;
calculating a frequency spectrum of each intrinsic mode function from the plurality of intrinsic mode functions;
selecting a threshold frequency;

summing up intrinsic mode functions whose frequency spectra are greater than the selected threshold frequency, to obtain the crackle-sound component; and summing up intrinsic mode functions whose frequency spectra are less than or equal to the selected threshold frequency, to obtain the respiration-sound component.

4. The lung-sound signal processing method according to claim 3, wherein the selected threshold frequency is located between 30 hertz and 50 hertz.

5. The lung-sound signal processing method according to claim 1, wherein the at least one time-domain feature parameter further includes at least one of: a quantity of crackle sounds at an early stage of the inspiratory-phase period, a quantity of crackle sounds at a later stage of the inspiratory-phase period, a quantity of crackle sounds within the inspiratory-phase period, and a ratio of a time duration of the crackle-sound signal to a time length of the inspiratory-phase period.

6. The lung-sound signal processing method according to claim 1, wherein the obtaining at least one feature parameter according to the crackle-sound signal, further includes: obtaining at least one frequency-domain feature parameter.

7. The lung-sound signal processing method according to claim 6, wherein the at least one frequency-domain feature parameter includes at least one of: a total energy of the crackle-sound signal, and ratios of energies of crackle sounds of respective sub-bands to the total energy.

8. The lung-sound signal processing method according to claim 7, further comprising:

obtaining a frequency spectrum function of the crackle-sound signal;

obtaining a total bandwidth corresponding to the crackle-sound signal based on the frequency spectrum function;

obtaining a plurality of sub-bands based on the total bandwidth; and calculating an energy of crackle sounds of each sub-band in the plurality of sub-bands.

9. A computer readable storage medium, configured to store computer instructions, the computer instructions, when executed by a processor, causing the processor to implement one or more operations including:

obtaining a lung sound signal from a lung sound signal detector;

decomposing the lung sound signal by using an empirical mode decomposition algorithm, to obtain a crackle-sound component and a respiration-sound component;

obtaining an inspiratory-phase period based on the respiration-sound component;

extracting a crackle-sound signal located in the inspiratory-phase period from the crackle-sound component; and obtaining at least one feature parameter according to the crackle-sound signal, wherein the obtaining at least one feature parameter according to the crackle-sound signal, includes: obtaining at least one time-domain feature parameter, the at least one time-domain feature parameter includes an ending time ratio (ETR) of an ending time of the crackle-sound signal to the inspiratory-phase period, wherein the ETR is calculated as:

$$ETR = \frac{T_{ending}}{T_{inspiration}}$$

wherein $T_{ending}$ denotes a time duration from a starting time of a stationary respiration cycle to a time when a last crackle sound appears within the inspiratory-phase period, $T_{inspiration}$ denotes a time duration of the inspiratory-phase period.

10. The computer readable storage medium according to claim 9, wherein the computer instructions, when executed by the processor, cause the processor to further implement an operation including:

classifying the crackle-sound signal based on the at least one feature parameter.

11. A lung-sound signal processing device, comprising one or more processors, the one or more processors being configured to run computer instructions so as to execute one or more operations including:

obtaining a lung sound signal from a lung sound signal detector;

decomposing the lung sound signal by using an empirical mode decomposition algorithm, to obtain a crackle-sound component and a respiration-sound component;

obtaining an inspiratory-phase period based on the respiration-sound component;

extracting a crackle-sound signal located in the inspiratory-phase period from the crackle-sound component; and obtaining at least one feature parameter according to the crackle-sound signal, wherein the obtaining at least one feature parameter according to the crackle-sound signal, includes: obtaining at least one time-domain feature parameter, the at least one time-domain feature parameter includes an ending time ratio (ETR) of an ending time of the crackle-sound signal to the inspiratory-phase period, wherein the ETR is calculated as:

$$ETR = \frac{T_{ending}}{T_{inspiration}}$$

wherein $T_{ending}$ denotes a time duration from a starting time of a stationary respiration cycle to a time when a last crackle sound appears within the inspiratory-phase period, $T_{inspiration}$ denotes a time duration of the inspiratory-phase period.

12. The lung-sound signal processing device according to claim 11, further comprising a classifier, the classifier being configured to classify the crackle-sound signal based on the at least one feature parameter.

13. The lung-sound signal processing device according to claim 12, wherein the classifier is configured to classify the crackle-sound signal based on the at least one feature parameter by using a tree-based method.

14. The lung-sound signal processing device according to claim 11, wherein the at least one feature parameter further includes a frequency-domain feature parameter.

15. The lung-sound signal processing device according to claim 11, wherein the at least one time-domain feature parameter further includes at least one of: a quantity of crackle sounds at an early stage of the inspiratory-phase period, a quantity of crackle sounds at a later stage of the inspiratory-phase period, a quantity of crackle sounds within the inspiratory-phase period, and a ratio of a time duration of the crackle-sound signal to a time length of the inspiratory-phase period.

16. The lung-sound signal processing device according to claim 14, wherein the at least one of the frequency-domain feature parameter includes at least one of: a total energy of the crackle-sound signal, and ratios of energies of crackle sounds of respective sub-bands to the total energy.

17. The lung-sound signal processing device according to claim 11, wherein the obtaining the inspiratory-phase period based on the respiration-sound component, includes:
    obtaining the stationary respiration cycle based on the respiration-sound component; and
    obtaining the inspiratory-phase period from the stationary respiration cycle;
    wherein the stationary respiration cycle includes an expiratory-phase period and the inspiratory-phase period.

18. The lung-sound signal processing device according to claim 11, wherein the decomposing the lung sound signal by using an empirical mode decomposition algorithm, to obtain the crackle-sound component and the respiration-sound component, includes:
    decomposing the lung sound signal by using an empirical mode decomposition algorithm, so that the lung sound signal is decomposed into a cumulative sum of a plurality of intrinsic mode functions;
    calculating a frequency spectrum of each intrinsic mode function from the plurality of intrinsic mode functions;
    selecting a threshold frequency;
    summing up intrinsic mode functions whose frequency spectra are greater than the selected threshold frequency, to obtain the crackle-sound component; and
    summing up intrinsic mode functions whose frequency spectra are less than or equal to the selected threshold frequency, to obtain the respiration-sound component.

19. The lung-sound signal processing device according to claim 11, wherein the selected threshold frequency is located between 30 hertz and 50 hertz.

* * * * *